United States Patent [19]
Andros

[11] Patent Number: 6,033,486
[45] Date of Patent: Mar. 7, 2000

[54] METHOD FOR CLEANING A SURFACE BY USING A CATIONIC SPONGE MATERIAL

[76] Inventor: Nicholas Andros, 913 W. Glenrosa, Phoenix, Ariz. 85013

[21] Appl. No.: 09/136,445

[22] Filed: Aug. 19, 1998

Related U.S. Application Data

[62] Division of application No. 08/677,130, Jul. 9, 1996, Pat. No. 5,844,030.

[51] Int. Cl.[7] .............................. A47K 7/02; A47L 13/40; B08B 3/04; B08B 6/00
[52] U.S. Cl. .................................... 134/6; 134/1; 134/26; 15/1.51; 15/1.52; 15/244.1
[58] Field of Search ...................... 134/1, 6, 26; 15/1.51, 15/1.52, 244.1

[56] References Cited

U.S. PATENT DOCUMENTS 5,311,634   5/1994   Andros ...................................... 15/97.1

*Primary Examiner*—Zeinab El-Arini
*Attorney, Agent, or Firm*—Parsons & Goltry; Robert A. Parsons; Michael W. Goltry

[57] ABSTRACT

A method of cleaning a surface including the steps of providing a cationic sponge material containing cationic radicals. Exposing particles and charges carried by the surface to be cleaned to the cationic radicals. Attracting and retaining particles and charges on the surface to be cleaned to the cationic radicals.

4 Claims, 6 Drawing Sheets

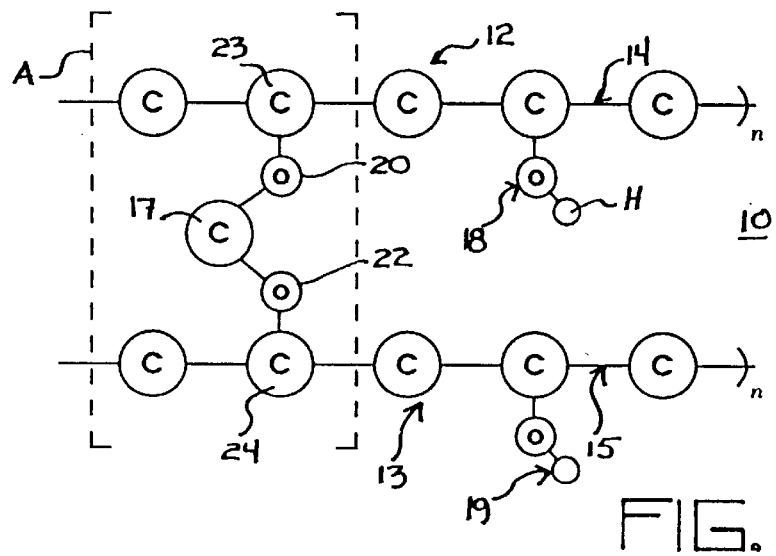
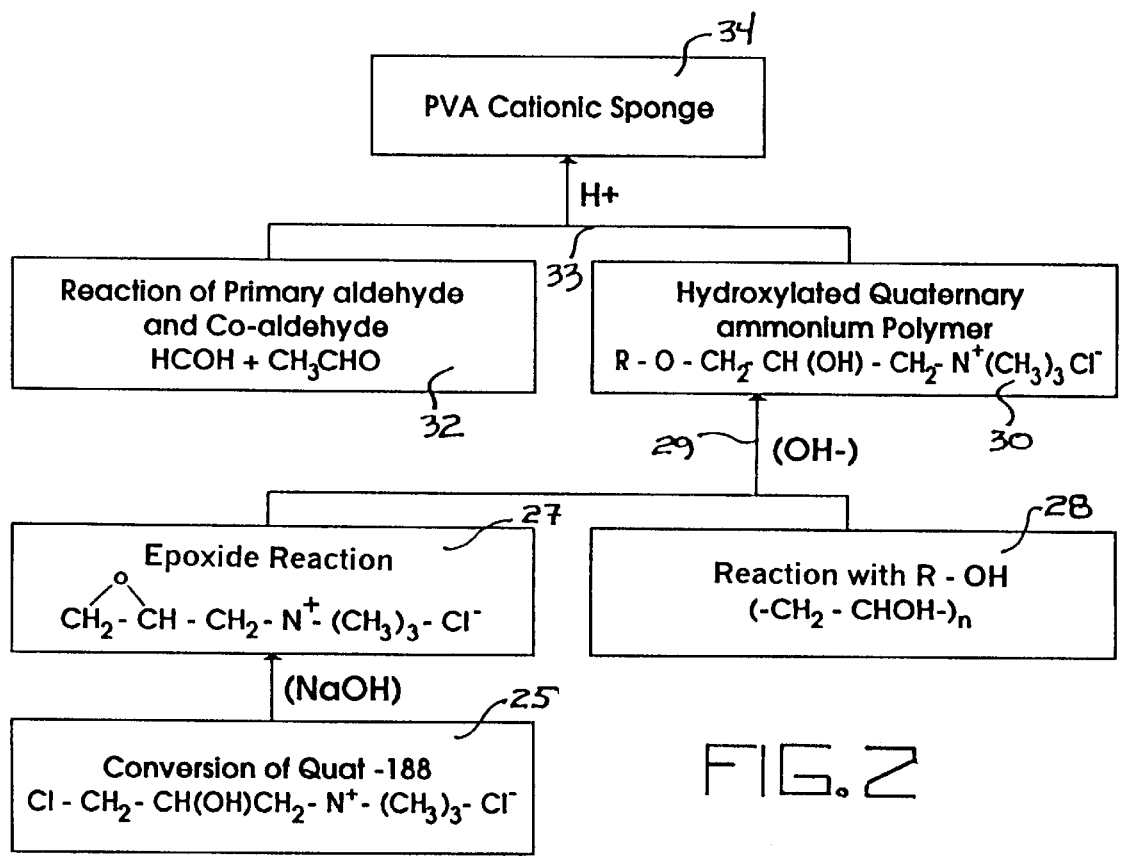
FIG. 1
FIG. 2

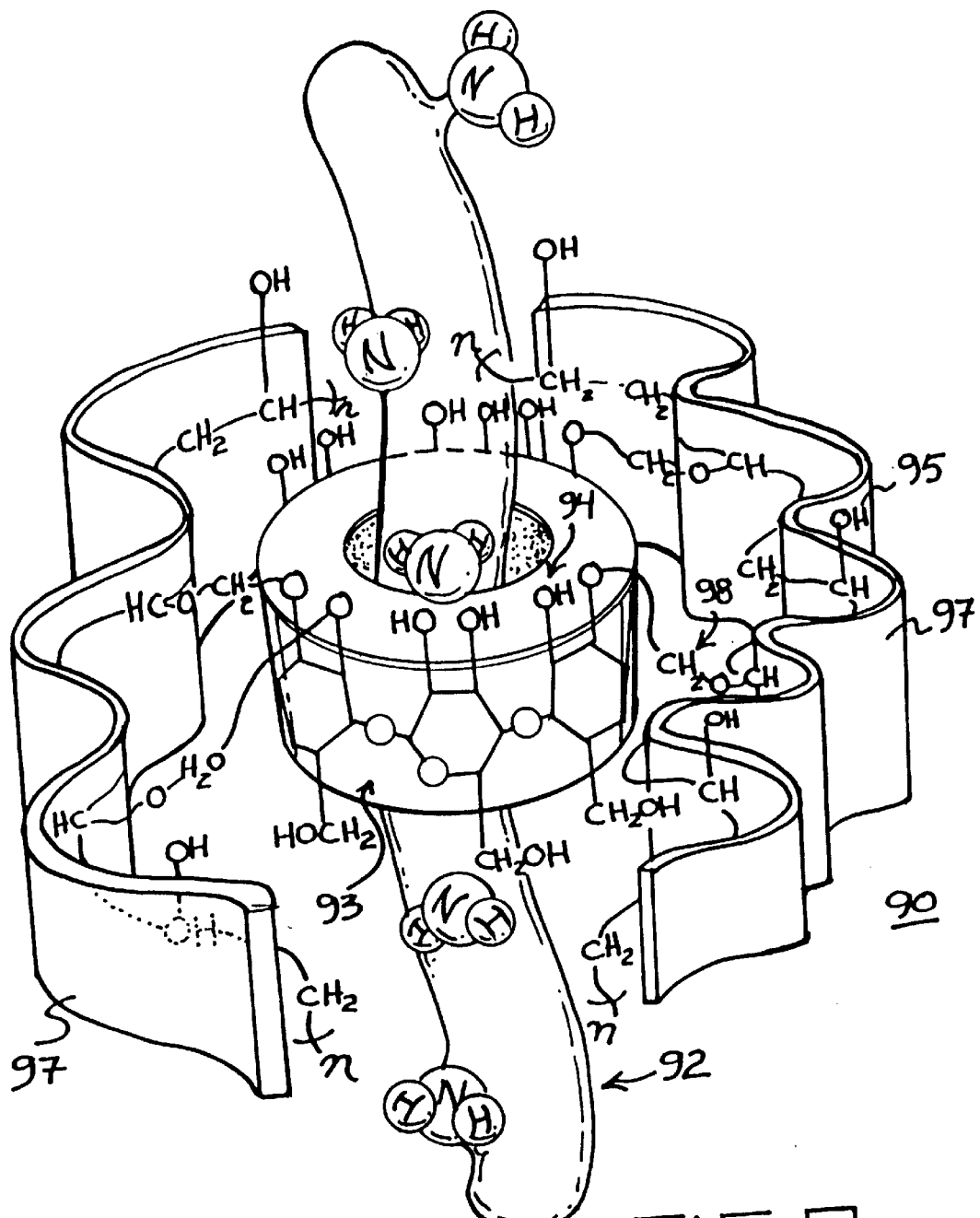

METHOD FOR CLEANING A SURFACE BY USING A CATIONIC SPONGE MATERIAL

This application is a division of application Ser. No. 08/677,130, filed Jul. 9, 1996, now U.S. Pat. No. 5,844,030.

FIELD OF THE INVENTION

This invention relates to cleaning systems.

More particularly, the present invention relates to differential physical chemical cleaning.

In a further and more specific aspect, the present invention concerns ionic sponge materials and a method of producing the same used in differential physical chemical cleaning systems for cleaning hydrophobic surfaces.

BACKGROUND OF THE INVENTION

Many industries today require the ability to efficiently clean highly finished surfaces, removing particles and other surface contaminants. Specific articles having highly finished surfaces include, but are not limited to, wafers of semiconductor material, and memory disks.

Semiconductor wafers must be cleaned prior to any processing steps used to produce semiconductor devices. Due to the fragile nature of semiconductor wafers, achieving a high degree of cleanliness, as well as a high yield of clean wafers is difficult. Many cleaning devices produce a low yield of clean wafers due to breakage or an unacceptable level of surface contaminants. Memory discs provide less of a problem with breakage, being more durable.

Currently, cleaning devices have been developed to overcome some of these problems. Devices for cleaning wafers generally consist of a cylindrical roller passing over a wafer. The cylindrical roller conventionally includes tufted nylon or other types of bristles extending from a central core. The bristle roller brushes are fixed horizontally and rotate as the wafer or memory disk is passed between the bristle surfaced brushes while the surfaces are copiously drowned in cleaning solution or de-ionized water.

Wafers cleaned in this manner are often unacceptable due to particles and other surface contaminants missed or passed over in the cleaning process. In addition, the softness of the bristles varies according to their composition, resulting in a heterogeneous mixture of bristles, each harder or softer than their counter parts. This results in breakage of the wafers as well as damage to wafer surfaces. Other drawbacks, resulting in unsatisfactory cleaning, may be attributed to the hydrophobic nature of bristle tufted brushes. The fiber surfaces of these brushes are never wetted, and require large amounts of de-ionized water or cleaning solution to work in the cleaning process.

Substantially more effective, are roller brushes formed from sponge material. Typically, roller type cleaning devices employ an outer layer of sponge material. While cleaning devices employing sponge material are effective in generally cleaning a surface by removing a great deal of particulate material and other surface contaminates, they are less effective in removing fine particles to provide a more extensively cleaned surface.

These mechanical scrubbing devices, however, are still deficient in their ability to clean the surfaces. The mechanical cleaning of wafers, memory discs and other electronic materials and substrates is deficient because substantially complete cleaning takes place at the molecular level and not at the mechanical level. Ultra-fine particles adhere to the surfaces of substrates by mechanical means and more importantly, by electrostatic forces. Attempting to remove these particles by mechanically washing the surface with brushes and conventional sponge material is often futile. When the size of a particle approaches sub-micron and amicron sizes, they take upon themselves a formal charge which is held to a hydrophobic surface by what is described as electrostatic or van der Waals forces. This well known phenomona is observed in many aspects of wafer and memory disk processing.

Removal of electrostatically attracted particles is almost impossible by conventional means. Various claims have been made that removal of ultra-fine particles can be achieved solely by controlling the porosity of micro-porous sponge devices used in the cleaning process. This cannot be substantiated, since cleaning of a hydrophobic surface entails many variables such as water pressure or solvent volume, forces applied upon the surface, surfactants and their polarity, interface relations between the hydrophobic surface and the hydrophilic surface and a host of physical/chemical variables. Therefore, conventional cleaning devices cannot provide the close cleaning a finely finished surface requires.

It would be highly advantageous, therefore, to remedy the foregoing and other deficiencies inherent in the prior art.

Accordingly, it is an object of the present invention to provide a new and improved sponge material.

Another object of the present invention is to provide an improved method of cleaning surfaces of articles.

And another object of the present invention is to provide an improved method of producing sponge material.

Still another object of the present invention is to provide a sponge material capable of removing ultra-fine particles including sub-micron and amicron sizes, from hydrophobic surfaces.

Yet another object of the present invention is to provide a sponge material capable of attracting charged particles.

Yet still another object of the present invention is to provide a cationic sponge material.

A further object of the present invention is to provide a system for removing undesirable particles.

And a further object of the present invention is to provide a material capable a attracting undesirable particles.

SUMMARY OF THE INVENTION

Briefly, to achieve the desired objects of the present invention in accordance with a preferred embodiment thereof, provided is a differential physical chemical cleaning system including a plurality of formally charged cleaning devices for engaging a surface to be cleaned and a fluid delivery system for delivering precipitating agents to the surface to be cleaned and the plurality of cleaning devices.

Further provided is an ionically charged sponge material for attracting and for retaining charged particles. The sponge material includes a plurality of ionic hydroxylated polymers cross-linked to a plurality of hydroxylated polymers.

The ionic hydroxylated polymer preferably includes cationic polyvinyl alcohol wherein the cationic polyvinyl alcohol includes formally cationically charged atoms.

Further provided is a method of forming cationic sponge material including the steps of forming a plurality of cationic hydroxylated polymers, forming a plurality of hydroxylated polymers, and cross-linking the cationic hydroxylated polymers and the hydroxylated polymers.

In a more specific method the step of forming the plurality of cationic hydroxylated polymers includes the step of forming an epoxide and reacting it with polyvinyl alcohol. Forming an epoxide includes reacting a quaternary ammonium complex with a metallic hydroxide.

Also provided is an ionically charged material for attracting and for retaining charged particles including a plurality of cross-linked hydroxylated polymers, a host molecule cross-linking the hydroxylated polymers, and a guest molecule having a high charge density carried by the host molecule.

BRIEF DESCRIPTION OF THE DRAWINGS

The foregoing and further and more specific objects and advantages of the instant invention will become readily apparent to those skilled in the art from the following detailed description of a preferred embodiment thereof, taken in conjunction with the drawings, in which:

FIG. 1 is a simplified schematic illustrating cross-linked PVA molecules forming a cleaning sponge;

FIG. 2 is a flow diagram illustrating the formation of a material for removing undesirable particles in accordance with the teachings of the present invention;

FIG. 9 is a perspective view illustrating a molecular model of a further embodiment of a material for removing undesirable particles.

DETAILED DESCRIPTION OF THE PREFERRED EMBODIMENT

Figure 3:
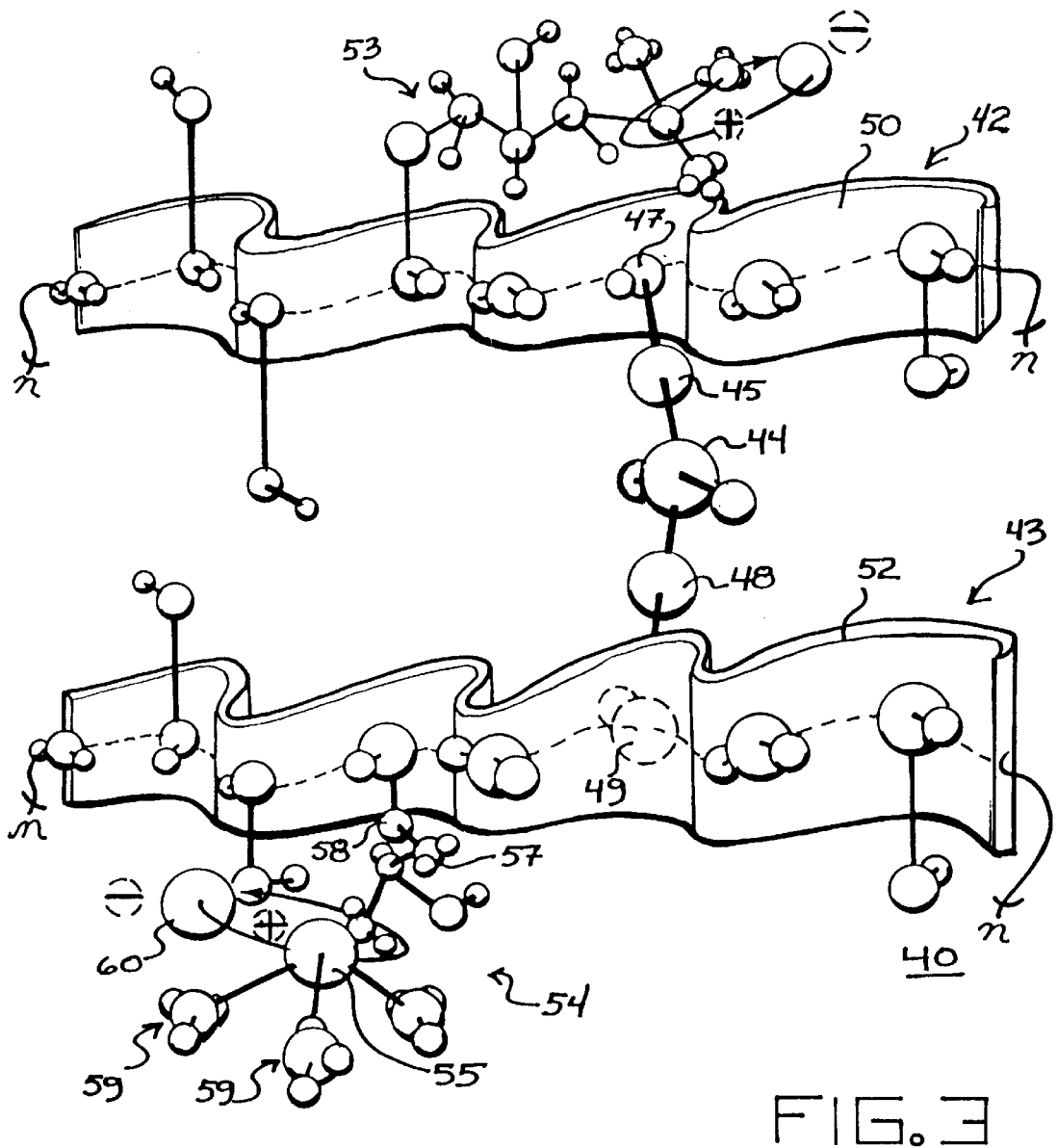
FIG. 3 is a perspective view illustrating a molecular model of a PVA molecule cross-linked with a cationic PVA molecule forming the material for removing undesirable particles of FIG. 2.

The present invention includes a differential physical chemical cleaning method for efficiently cleaning highly finished surfaces, removing particles and other surface contaminants. Specific articles having highly finished surfaces include, but are not limited to, wafers of semiconductor material, and memory disks. Differential physical chemical cleaning employs one element or feature of one cleaning device, using its characteristic traits to work with one or more elements whose characteristic traits may be similar or dissimilar, to produce a cleaning effect by reason of quantitative and qualitative differences.

In silicon wafers, for instance, the silicon atoms can be described by analogy as being afloat in a sea of electrons, having a formal charge upon its surface. As polishing or cleaning takes place, each successive wave of polishing or cleaning upon its surface brings a new wave of electrons to formally recharge the wafer surface. The ideal situation is to remove the shear-plane by electrical or mechanical means. The next step is to remove the counter-ions, ions which may damage the surface of the silicon wafer. To achieve the ideal situation, a cationic polyvinyl alcohol sponge of fine micropores, whose porosity is preferably in the range of between 10 and 110 microns of pore size is used as a cleaning device in a differential physical chemical cleaning system.

The formation of a micro-porous sponge is accomplished by cross-linking an hydroxylated polymer, preferably polyvinyl alcohol (PVA), and adding a surfactant to produce the desired cell structure and properties. PVA is cross-linked by employing a cross-linking agent such as an aldehyde, a poly basic acid, a ketone or other molecule. The variety of cross-linking agents allows the physical properties of the sponge to be modified as desired. Different cross-linking agents can be employed to vary the hydrophilicity, flexibility, softness or hardness, and other characteristics of the sponge.

Turning now to the drawings in which like reference characters indicate corresponding elements through the several views, attention is first directed to FIG. 1 which illustrates the cross-linked molecules in PVA sponge material, generally designated 10. PVA sponge material 10 consists of cross-linked polyvinyl alcohol (PVA) molecules. The preferred method of forming micro-porous sponge material is by cross-linking PVA molecules with a cross-linking agent in the presence of an acid catalyst. Still referring to FIG. 1, a PVA molecule 12 is cross-linked to a second PVA molecule 13 in the area enclosed by broken line A. To aid in understanding the figures, carbon atoms are designated with a C, oxygen atoms with an O, and hydrogen atoms with an H. Some hydrogen atoms have been omitted for clarity. Molecules 12 and 13 consist of backbones 14 and 15 respectively, being a plurality of carbon atoms to which hydroxyl groups are bonded. The cross-linking agent provides a carbon atom 17 which bonds between hydroxyl groups, such as hydroxyl group 18 and 19 of molecules 12 and 13 respectively, giving off a molecule of water. Each hydroxyl group is composed of an oxygen atom and a hydrogen atom. Carbon atom 17 bonds to an oxygen atom 20 bonded to a carbon atom 23 of backbone 14 and to an oxygen atom 22 bonded to a carbon atom 24 of backbone 15, displacing hydrogen atoms (not shown) and forming the cross-link. Further details of this reaction and structure have been omitted since it will be well understood by one skilled in the art. One skilled in the art will further understand that a large number of these cross-links, between a myriad of PVA molecules, occur to form a micro-porous sponge.

It has been determined that most effective means of removing ultra-fine particles from hydrophobic surfaces, such as the surfaces of semiconductor wafers and memory disks, is by attracting and retaining the particles. PVA sponges are inadequate for this purpose, relying solely on mechanically removing particles. The electrostatic force or van der Waals force which binds fine particles to a hydrophobic surface are not easily or satisfactorily overcome by mechanical means.

Cationic sponge is created according to the teachings of the present invention, by cross-linking an hydroxylated polymer, preferably a PVA molecule to a cationic hydroxylated polymer, preferably a cationic polyvinyl alcohol molecule, thereby forming a micro-porous sponge material capable of attracting and removing charged particles, including ultra-fine particles. Formation of the cationic sponge consists of first forming cationic PVA. This is accomplished by forming an epoxide and reacting it with PVA to produce cationic PVA.

Referring now to FIG. 2, a flow chart of the formation of cationic sponge is illustrated. The first step, as shown in box 25, is reacting a quaternary ammonium complex with a metallic hydroxide. In this preferred embodiment, the quaternary ammonium complex used is N-(3-chloro-2-hydroxypropyl) trimethylammonium chloride supplied by Dow Chemical as Quat-188, and the metallic hydroxide is sodium hydroxide. The resulting epoxide 2,3-epoxypropyltrimethylammonium chloride is illustrated in box 27. An hydroxylated polymer, in this embodiment a PVA molecule, is illustrated in box 28. The hydroxylated polymer of box 28 is reacted with the quaternary ammonium complex of box 27 at a basic pH. The resulting hydroxylated quaternary ammonium polymer is depicted in box 30 and is preferably cationic PVA, a branch polymer of PVA. Box 32 represents a cross-linking agent such as an aldehyde, a poly basic acid, a ketone or other poly-functional molecules. In this embodiment an aldehyde, specifically formaldehyde, and a co-aldehyde, specifically acetaldehyde, are used to illustrate that multiple cross-linking agents may be used. The cross-linking agent/agents of box 32 are reacted with the hydroxylated quaternary ammonium polymer of box 30 in the presence of an acid catalyst depicted by arrowed line 33 to form the PVA cationic sponge designated by box 34. While substantially any acid catalyst may be used, the preferred acid catalyst is sulfuric acid. It will be understood that a solution of pure cationic PVA is impractical, therefore, it will be assumed that both cationic PVA and PVA are present in the cross-linking step. Additional PVA may also be added, with the resulting sponge being less cationically polar as more PVA is used.

As can be seen with reference to FIG. 3, cationic sponge material generally designated 40, includes a plurality of cross-linked cationic PVA molecules. To aid in understanding the figure, carbon atoms are designated with a C, oxygen atoms with an O, and hydrogen atoms with an H. Some hydrogen atoms have been omitted for clarity. Illustrated is a cationic PVA molecule 42 and a cationic PVA molecule 43 cross-linked by a methylene bridge. For purposes of illustration, sponge material 40 is shown by cationic PVA molecule 43 cross-linked to cationic PVA molecule 42. However, as discussed above, cationic PVA may cross-link to PVA, and residual or added PVA molecules. The cross-link is substantially similar to the cross-link of FIG. 1, with a cross-linking agent providing a carbon atom 44 which bonds between hydroxyl groups, giving off a molecule of water. Carbon atom 44 bonds to an oxygen atom 45 bonded to a carbon atom 47 of molecule 42 and to an oxygen atom 48 bonded to a carbon atom 49 of molecule 43, displacing hydrogen atoms, and forming the cross-link.

Cationic sponge material 40 differs from conventional sponge material in that molecules different than PVA molecules, namely cationic hydroxylated quaternary ammonium polymers, are cross-linked. Cationic PVA molecules 42 and 43 each include a backbone 50 and 52 respectively, composed of a plurality of carbon atoms to which hydroxyl groups are coupled, and further include a polymer branch 53 and 54 respectively. As the polymer branches are identical, only polymer branch 54 will be described in detail. Polymer branch 54 terminates with a nitrogen atom 55 providing the positive charge. Polymer branch 54 is coupled to backbone 52 by a carbon atom 57 bonded to an oxygen atom 58 which is in turn bonded to backbone 52. A plurality of methyl groups 59 are bonded to nitrogen atom 55, and a chlorine atom 60 is loosely bonded to nitrogen atom 55 by electrostatic forces. This bond is easily interrupted by charged particles which are attracted to and retained by nitrogen atom 55.

Examples of method of forming cationic PVA (See FIG. 2 flow diagram for the production of Cationic sponge), include:

EXAMPLE 1

Formation of PVA Solution

With the aid of a measuring device such as a graduated cylinder, carefully add 1000 ml of cold de-ionized (D.I.) water to a jacketed kettle and slowly add 150 grams of 98% hydrolyzed Polyvinyl alcohol (PVA) with constant mechanical stirring, until all the PVA is suspended in the water. A slurry will appear. Adjust the temperature by raising the jacket to 80–90° C. and allow the PVA solids to dissolve, producing a viscous solution. Continue to stir the PVA solution and add 0.5–1.0% non-ionic surfactant till the cloud point appears in the PVA solution. Cool the entire contents of the kettle to 33° C. and determine the viscosity. Adjust the viscosity to 2300–2500 CP determined at 33° C.

10% Sodium Hydroxide Solution

To a 500 ml round bottom flask surrounded with an ice-bath, add 125 ml of DI water and slowly add 25 grams of reagent NaOH pellets. After all the NaOH has dissolved, add an additional 125 ml of DI water. Stir till homogeneous. Stopper to exclude $CO_2$.

Epoxide Formation

To a 500 ml round bottom flask, add 160.3 grams of 3-chloro-2-hydroxypropyl trimethylammonium chloride, and 4 drops of Alizarin yellow. Slowly add the sodium hydroxide solution described above and cool the flask to 50° C. After the NaOH is added, heat the flask to 50° C. and maintain this temperature for 15 min. Cooling the reaction if necessary. Adjust the pH to 12.0, the Alizarin yellow will turn to violet. The reaction will take place as the pH drops. After the reaction is over, the pH will drop to 10.1, and the solution will turn to light yellow at pH 10.1. It should be noted that it may not be necessary to use all the 10% NaOH solution.

Cationic PVA Formation

To the PVA solution the formation of which was described previously, slowly add all of the epoxide formed above with constant stirring until all of the epoxide is dispersed into the PVA solution. Predetermined the viscosity of the mixture and adjust the viscosity of the mixture to approximately 2300–1500 CP by heating to evaporate water. Maintain the pH in a range of 10.1–10.5. A pH of 10.5 should not be exceeded. Continue to cook the mixture with constant stirring for 6 hours at 60° C., in a constant temperature jacketed kettle or water bath.

At the end of the 6 hour period, neutralize the PVA solution with 2 N $H_2SO_4$ solution to pH 6.0. The resulting Cationic PVA can be filtered in a medium glass filter frit. Wash with 550 ml. of DI water to remove all traces of $H_2SO_4$.

EXAMPLE 2

Insitu Process

The following is an example of the formation of Cationic PVA insitu. The procedure of Example 1 is repeated with the following exceptions:

At the end of the 6 hour cooking period, the mixture is neutralized with 2 N $H_2SO_4$ solution to pH 6.0. At this point the mixture is cooled to 33° C. and the viscosity is determined. The viscosity of the solution is adjusted by evaporation at 45–50° C., with constant stirring, till a viscosity of the Cationic PVA solution reaches 2500 CP when measured at 33° C. using a Brookfield Viscometer, Model LVF No. 4 Spindle.

The cationic PVA solution is cooled to room temperature and poured through a filter screen to remove clumps which may have occurred. This reagent can be stored at 43° C. and utilized to make sponge products.

Sponge Formation with Cationic PVA

The final cationic products of examples 1 and 2 are now acetylated with 37% Formaldehyde solution as follows:

To 1000 ml. of Cationic PVA solution whose viscosity's have been adjusted to 2300–2500 CP., the PVA solution is vigorously frothed to a maximum rise, at which time 100 ml. of 37% Formaldehyde solution is added. It should be noted, that any low molecular weight aldehyde may be added to this reaction to acetylate the PVA. The frothing is continued till a stable froth appears. The mixture is now catalyzed with 28% $H_2SO_4$ mixed well, and the entire mixture is poured into a suitable mold. The mold is cured for 24 hours, at 115–120° F., and then de-molded. The sponge is neutralized, washed to extract all reagents, and finally used to clean silicon wafers and memory discs. The sponge contains a formally charged Nitrogen atom on the backbone of the PVA polymer.

Figure 4:
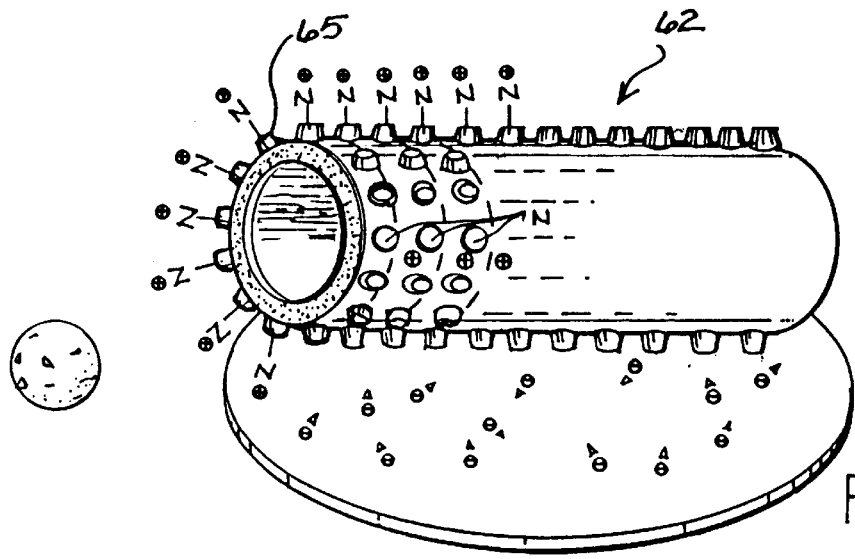
FIG. 4 is a perspective view illustrating a cationic sponge roller as it would appear proximate a hydrophobic surface.
Figure 5:
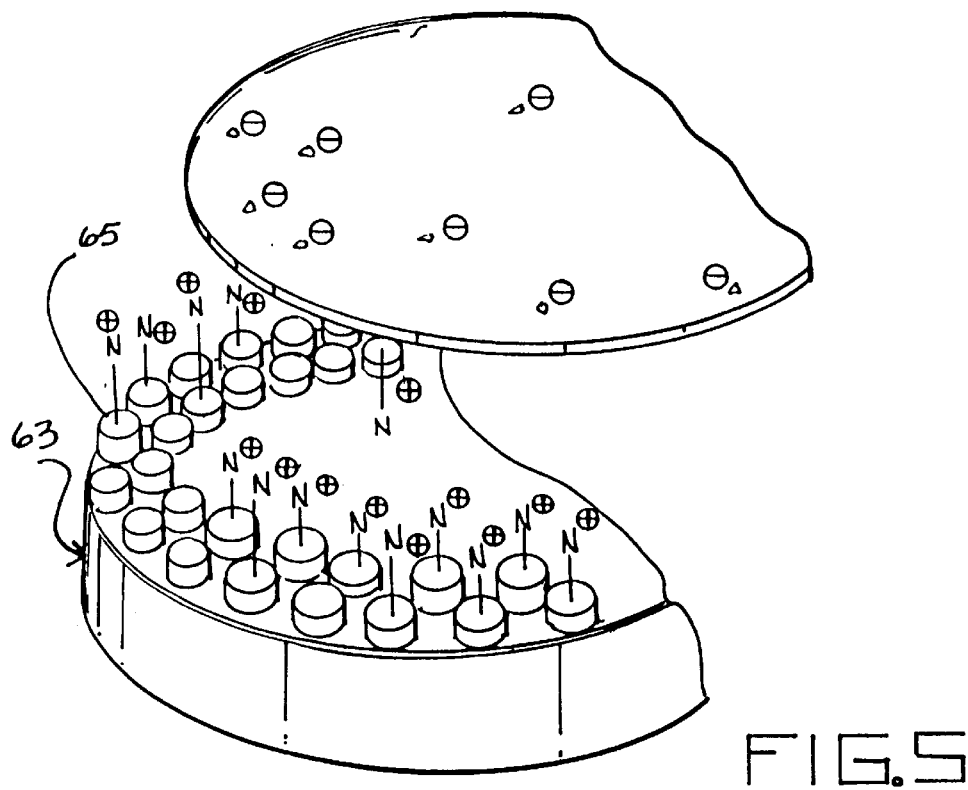
FIG. 5 is a perspective view illustrating a cationic sponge cleaning disk as it would appear proximate a hydrophobic surface.
Figure 6:
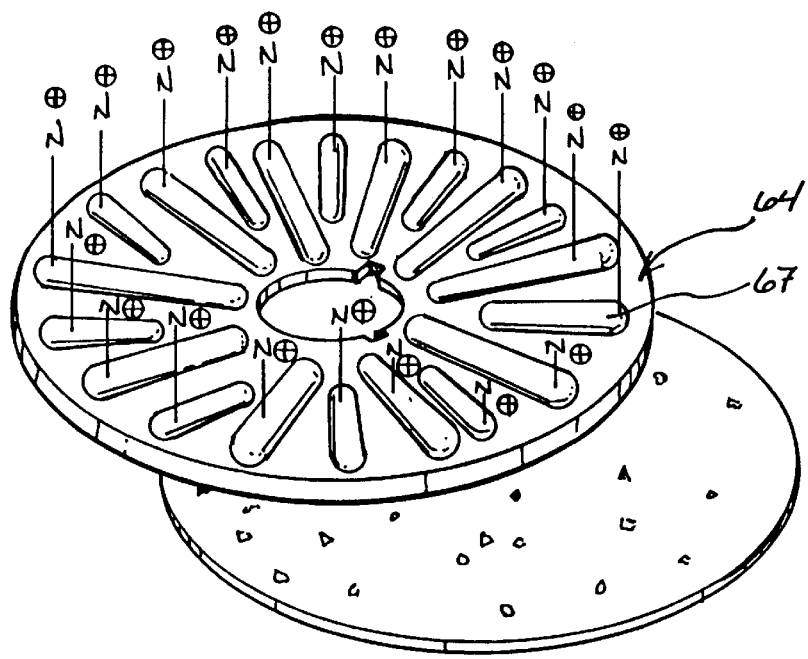
FIG. 6 is a perspective view illustrating a cationic sponge cleaning pad as it would appear proximate a hydrophobic surface.
Figure 6:

Turning now to FIGS. 4–6, various configurations of sponge brushes, also referred to as cleaning devices, constructed of cationic sponge material produced in accordance with the present invention previously described, are illustrated. FIG. 4 shows a roller type sponge brush generally designated 62, FIG. 5 shows a disk type brush generally designated 63, and FIG. 6 shows a two sided disk type brush generally designated 64, each positioned for cleaning a surface of an article such as a semiconductor wafer or memory disk. Brushes 62, 63, and 64 each preferably include a plurality of nubs 65 extending from an outer surface, or other projections such as ribs 67 of FIG. 6. Nubs 65 and ribs 67, having cationic radicals provided by the structure of the sponge material discussed infra, contact the surface to which a plurality of charged particles adhere. For purposes of this disclosure, charged particles include any material which is naturally polar and particularly, particles approaching sub-micron and amicron sizes which take upon themselves a formal charge. It will be understood that particle may also be materials which are naturally polar and are a micron or more in size. As the sponge brush engages the surface, particles are attracted to and retained by the cationic radical in the sponge material, thereby being removed from the surface.

Cationic cleaning sponge are not restricted in their geometry to rollers, brushes, circular or flat pads and disks or combinations thereof, or any particular configuration upon the surface of the sponge device. Cationic cleaning sponges are also not restricted to specific ranges of porosity, pre size or hardness. The principle of attracting charged particles to a cationically charged sponge body is therefore not dependent upon a geometry of configuration of that sponge body.

The nubbed surfaces and the geometric forms such as a ribbed surface contain in their molecular structure the formally charged nitrogen atom. The mechanical abrasion and contact with the surface of the silicon wafer essentially attracts negatively charged particles to the cationic surface of the sponge. At the shear plane, a potential is formed, i.e., the electrokinnetic or zeta potential. It is generally assumed that the zeta potential and electrokinnetic are the same. If this is so, though many other factors enter this model, as a first approximation it becomes possible to remove the diffuse layer (mobile layer) of contaminants by the cationic abrasion of a formally charged PVA sponge. Effectively, the cationically charged PVA sweeps the negatively charged particles from the shear plane, attracting these particles to the cleaning sponge. The use of suitable surfactants releases the remaining particles from the shear plane into solution.

It is assumed that the charge density on the surface of the wafer remains constant under all conditions; in fact, as the conditions of the surface are altered, i.e., by increasing the concentration of electrolyte, or the two surfaces are brought together into very close distances, 1–2 microns, the number of "free" charges on the surface may be reduced as result of the specific absorption of ionic contaminants of opposite charge. Thus as the two charged surfaces are brought together by the cationic PVA and the silicon wafer, the surface charge density becomes a function of the distance of separation, and tends towards zero at contact. This phenomena is sometimes referred to as "CHARGE REGULATION". The end effect of the Charge Regulation is to reduce the electrical potential of the surface; reduce the "thickness" of the electrical double layer and reduce the effective repulsion between the surfaces. The chemically charged PVA acts as one charged surface, being brought to the surface of the silicon wafer with its surface charge density. This is believed to be the mechanism of how the cleansing takes place upon the surface of the wafer.

In general in the beginning of the cleaning process, there is little electrostatic repulsion to hinder the close approach of particles, thus dirt and contamination build up on the surface of the wafer, possibly a cause of haze, as a consequence of the van der Walls forces. When the ionic strength is increased in the cleaning process, by the addition of ions, particularly those of high ionic charge type, such ions act as precipitating agents, Schulze-Hardy rule, and since hydrophobic particles are precipitated most efficiently by ions of opposite charge and high charge number, it follows that the reverse would be true for hydrophyllic surfaces.

As will be readily appreciate by one skilled in the art, a cationic sponge body employed to collect charged particles will eventually become filled. In other words all of or a substantial amount of the cationic radicals of the cationic sponge body will have a charged particle bound thereto and rendered neutral. This could require replacement of the cationic sponges at an undesirable rate, especially if the surfaces being cleaned were exceptionally dirty. While the sponges are extremely effective, their lifetimes can be increased by providing for reactivation of the cationic radicals by removing the charged particles. This can be accomplished in a number of different manners, such as by removing the sponges from the cleaning apparatus and washing with charged solutions to remove the charged particles by precipitation. This however, is not as effective as providing a cleaning system which does not require the removal of the sponges.

A differential physical chemical cleaning system, capable of taking advantage of the charge density differences on the surfaces of the cleaning sponges and removing the charged particles captured by the sponges, includes sponge materials whose molecular structures contain formally charged atoms or molecules and other cleaning materials of similar or dissimilar charged atoms or molecules. See Tables II, IV & V below.

A series of cleaning materials can also be incorporated in the system having compositions and physical properties as described in Tables I & II. The system can use multiple stages of mechanical rollers brushes and combinations thereof, as well as suitable solutions, as outlines in Tables I & II and exemplified by FIGS. 7 and 8.

TABLE I

Types of PVA Cleaning Devices Consisting of Brushes or Rollers 1.1 Rollers of two different porosities and two different materials.

1.2 Rollers of two similar porosities and two different materials.

1.3 Rollers of two different porosities, and two similar materials.

1.4 Rollers of two similar porosities and two similar materials.

TABLE II

Combinations of Porosities and Materials 1.1=AB
1.2=CB
1.3=AD
1.4=CD

TABLE III

PVA Cleaning Devices That Use One, Two, or More Rollers of Charge Density Combinations 3.1 Roller or Brushes with a negative charge density (−) (−)

3.2 Rollers or brushes with a positive charge density (+) (+)

3.3 Rollers or brushes with a neutral charge density, and a negative charge density (0) (−)

3.4 Rollers or brushes with a neutral charge density and a positive charge density (0) (+)

3.5 Rollers and brushes with a negative charge density and a positive charge density (−) (+)

TABLE IV

| CHARGE DENSITY COMBINATIONS | |
| --- | --- |
| Charge Sign | Combination |
| (−) | (−) (−) Anionic Anionic |
| (+) | (+) (+) Cationic Cationic |
| (0) | (0) (−) Neutral Anionic |
|  | (0) (+) Neutral Cationic |
|  | (−) (+) Anionic Cationic |

TABLE V

| | | | |
| --- | --- | --- | --- |
| AB (−) (−) | CB (−) (−) | AD (−) (−) | CD (−) (−) |
| AB (+) (+) | CB (+) (+) | AD (+) (+) | CD (+) (+) |
| AB (0) (−) | CB (0) (−) | AD (0) (−) | CD (0) (−) |
| AB (0) (+) | CB (0) (+) | AD (0) (+) | CD (0) (+) |
| AB (+) (−) | CB (+) (−) | AD (+) (−) | CD (+) (−) |

TABLE VI

| REAGENT NOMENCLATURE | |
| --- | --- |
| Reagent | Description |
| A | pH reagents or misc. Buffers in combination with H+ or OH− |
| B | Cationic Reagents (+) |
| C | Neutral Reagents (0) |
| D | Anionic Reagents (−) |
| E | Water (aqueous) and or non aqueous diluents |

Figure 7:
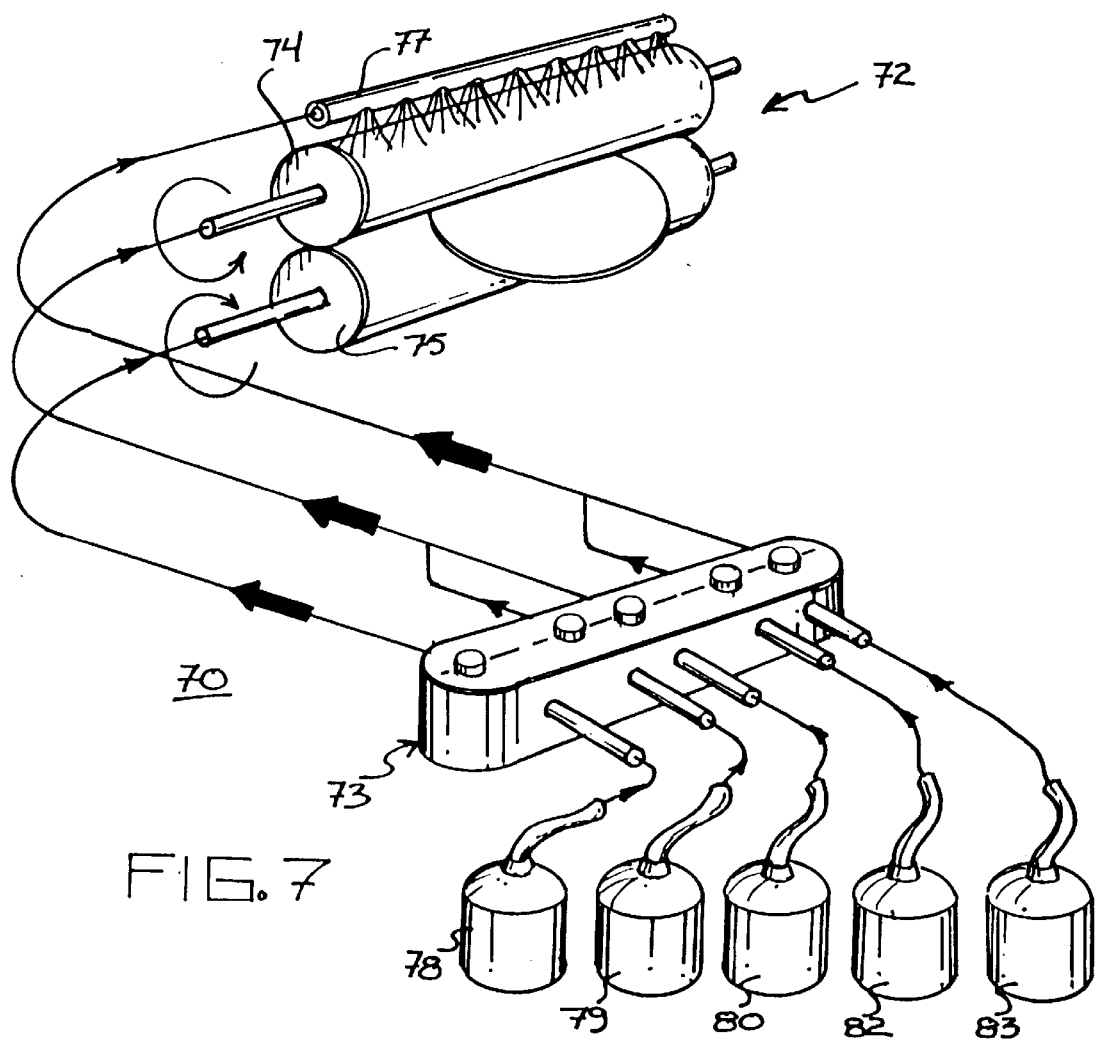
FIG. 7 is a simplified schematic in perspective, illustrating a single stage with associated fluid supply of a multi-stage cleaning system.

Turning now to FIG. 7, portions of a differential physical chemical cleaning system 70 for cleaning surfaces of disks and wafers is illustrated. The system can include one or a plurality of stages 72, each supplied by a multi-channel delivery pump 73. Each stage 72 includes a pair of sponge roller brushes 74 and 75 and a stationary irrigation dispenser 77 for providing a curtain of washing solution. While a curtain of solution is applied, it will be understood that the solution can be supplied in any conventional manner such as spraying, flooding etc.

Additional solutions are supplied from multi-channel delivery pump 73 to the interior of sponge roller brushes 74 and 75. The solutions include pH reagent or miscellaneous buffers 78, a cationic reagent 79, a neutral reagent 80, an anionic reagent 82 and a diluent 83. The different solutions aid in the cleaning process by acting as precipitating agents and renew the ionic radical in the material of the sponge brush so that it may be used for extended periods. Multi-channel pump 73 is capable of adjustably delivering charged reagents and diluents to the sponge rollers at differing flow rates and mixtures. By adjusting the flow and mixture of the reagents to alter the colligative properties such as pH, i.e., the hydrogen ion concentration of the wash solution, the concentration of Cationic, Anionic or Neutral reagents, or their mixtures thereof, the various contaminants upon the surface of the wafers or memory discs may be gradient eluted. Thus, selectively removing the contaminant whose ionic charge are most susceptible to chelation, scavenging, charge modification, absorbence, etc. while binding to the PVA sponge.

Figure 8:
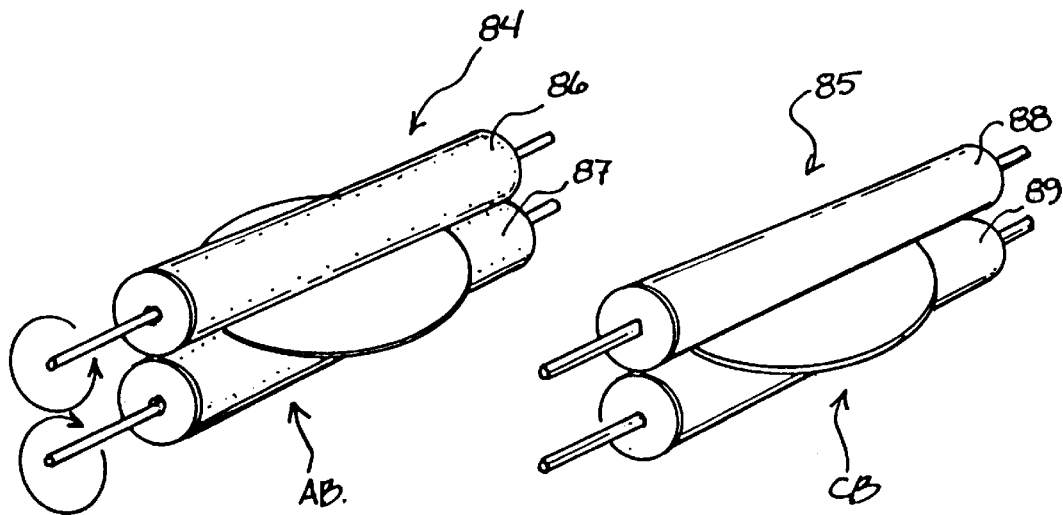
FIG. 8 is a perspective view illustrating a portion of the different stages of the multi-stage cleaning system of FIG. 7.

Different combinations of different types of material, different porosity, and different ionic charge of the sponge brushes can be employed for each different station, with the appropriate solutions applied as desired. Turning to FIG. 8, a portion of system 70 is shown. Specifically, stations 84 and 85 each include a pair of sponge brushes 86 and 87, and 88 and 89 respectively. For purposes of illustration, pair 86 and 87 are designated AB from table II, meaning that the brushes are of two different porosities and two different materials. Pair 88 and 89 are designated CB from table II, meaning that the brushes are of two similar porosities and two different materials. Additional stations can be employed using other combinations, including AD and CD from table II. In this manner very clean surfaces can be provided.

In a further embodiment of a sponge material, the sponge material is configured to hold a plurality of molecules having a high charge density. The sponge material has the ability to act as a "host" capturing a formally charged molecule "guest," and releasing the guest selectively and conditionally as the properties of the cleaning solution are changed; e.g., pH, temperature, concentration, etc.

Turning to FIG. 9, such a molecular sponge material, generally designated 90, is illustrated. Typical molecules of very high charge density are represented by the guest compound Polyethylenimine (PEI) 92 carried by the host molecule, preferably Cyclodextrin 93. PEI molecules have the highest cationic charge density of any known organic polymer, about 17–23 meq./gram.

To fulfill the requirements of PVA sponge cleaning brushes capable of containing a GUEST, whose molecular structure could encapsulate a high charged density amine such as PEI, free hydroxyl groups 94 of Cyclodextrin 93 are first cross-linked to available hydroxyl groups 95 of PVA molecules 97. This is accomplished by forming methylene bridges 98 between Cyclodextrin 93 and the PVA molecule 97 by use of a suitable aldehyde(s) such as formaldehyde. The methylene bridge is not described in detail, as it has been described previously in connection with cationic sponge material 40.

Once the methylene groups cross-link cyclodextrin molecule 93 to PVA molecule 97, the PVA now has incorporated into its structure a host molecule which can carry a guest. In this preferred embodiment the guest is Polyethylenimine 92, whose structure contains a high charge density of 17–23 meqs/gram. In effect, the PV now hosts the highly charged polyethylenimine. After extended use, if the PEI becomes saturated with charged particles, it can be induced to leave the host by changes in the environment. For example when used in cleaning system, a pH solution can be used which changes the pH in the environment, causing the PEI to be released. The sponge can now be "recharged" with new PEI. Alternatively, the PEI can be induced to release the material it has collected without leaving the host. The possibilities for the use of PEI carried within a porous medium such as the described host sponge are practically limitless.

As with the previously described embodiment, the porosities and degrees of softness and harness of the cleaning sponges and brushes are controlled by the amount of mixed aldehydes utilized to cross-link the hydroxyl groups, thus the degree of acetylization, controls these physical properties. Those familiar with the art are well versed in this technique.

In use, a host sponge containing PEI guests scavenges heavy metals, gases such as carbon dioxide, nitrogen oxides, halogens and volatile organic and other dissolved water born impurities. The process can be reversed to reclaim valuable metals by adjusting the pH.

Examples of methods of forming host PVA include:

EXAMPLE 1

To 250 m. of hot (35° C.) 98% hydrolyzed PVA solution, is slowly added, with continuous stirring, 3.75 grams of b-Cyclodextrin powder. The stirring is continued until all the b-Cyclodextrin is dissolved. The mixture is cooled to room temperature and quickly frothed by vigorously agitating with a high speed, high shear mixer. A rise of 1:1.25 is allowed to form, ten 25 ml of 37% Formaldehyde solution is added while the mixture is vigorously agitated.

The cyclodextrin tends to suppress the froth. Twenty-five ml of 30% Sulfuric Acid catalyst is added to the mixture, and again vigorously stirred. Finally, the mixture is poured into a suitable mold, and cured at 115–135° F. for 24 hours. After curing, the mass is cooled to room temperature and removed from its mold. The resulting sponge is neutralized in de-ionized (DI) water and Sodium bicarbonate solution. The sponge is thoroughly extracted in DI water to remove all traces of formaldehyde solution.

The porosity of the product is determined before going to the impregnation step with PEI. The porosities of acetylated b-Cyclodextrin/PVA best suited for impregnation are found to be between 50–90% preferably 60—60% with open cells formed, whose diameters are between 10–120 microns. The "Apparent Densities" of 0.275–300 gr./cc were determined with cell volumes in pores with diameters of 0.34–0.40 cc greater than 100.0 microns, and volumes in pores with diameters between 10.0 and 100.0 microns of 0.20–0.24 cc/cc. Any combination of the above may be formed but it is desired to construct narrow ranges of pore sizes between 30–120 micron diameter for optimum impregnation with PEI.

Impregnation with PEI

All traces of free Formaldehyde is removed in the above procedure since the formaldehyde will react with the PEI reducing the efficiency with which the PEI molecules bind to anions in the process of cleaning silicon wafers or memory discs.

The cleaning sponge that has been formed is now squeezed as dry as possible from its extraction bath or DI water and placed into a bath of 10–17% Polyethylenimine, whose molecular weight lies between 500,000–750,000 After a suitable period of saturation 2–25 hours, the sponge is removed, squeezed to remove excess liquid and is the air dried or stored damp.

It should be noted that b-Cyclodextrin acts as both a pore forming reagent, controlling pore size formation in the PVA sponge and as a cross linking Host Molecule to PVA through its acetylization to the PVA molecule. In effect the Host Portion of the cyclodextrin now allows the PEI to become the guest in the PVA-Cyclodextrin sponge. The resulting sponge material has a porosity of 57%, with a total surface area of 0.030 $m^2$/cc, and a bulk density of 0.27 gr/cc.

EXAMPLE 2

To 1000 ml of a 15% PVA solution, 98% hydrolyzed, containing 0.2% nonionic surfactant is added 75 grams of b-Cyclodextrin. The mixture is slowly stirred until all the b-Cyclodextrin is dispersed into the PVA. The mixture is frothed until the highest possible rise is obtained, in this case about 1:1.5. One hundred m. of 37% Formaldehyde solution is added and the frothing is continued until a stable rise is formed, and then 100 ml of 28% Sulfuric Acid is slowly added while mixing. The mixture is poured into a mold and cured for 24 hours at 115–150° F. Upon cooling the mold after 24 hours of cure, the resulting sponge is extracted in Sodiumbicarbonate solution until all the Sulfuric Acid is neutralized. The sponge is further extracted in DI water for 24 hours or greater to remove all traces of Formaldehyde.

In this example, the product produced is rigid to support impregnation with PEI solution for use in metals extraction.

EXAMPLE 3

To 1000 ml of 15% PVA solution containing 150 gr. of 98% hydrolyzed Polyvinyl Alcohol is added 50.0 grams of b-Cyclodextrin until totally dissolved into the PVA solution. Continue to stir since upon standing the viscosity of the final solution will rise from 2000 to 7000 CP if allowed to stand overnight.

Froth the above mixture until the highest possible rise occurs, then add 100 ml of 37% Formaldehyde solution, and continue to froth until a stable rise occurs. Catalyze the mixture with 100 ml of 30% Sulfuric acid solution; mix well for one to two minutes and immediately case into a suitable mold, and cure for 24 hours at 130° F. Upon cooling, the sponge is removed from the mold and neutralized in 15% Sodium bicarbonate solution to pH 7.0. Extract in DI water until all the traces of Formaldehyde are removed.

This example produces a soft highly micro-porous sponge with a porosity of 62.8%, and a Total Surface Area of 0.03 $m^2$/cc, having a Bulk Density of 0.29 gr./cc. The sponge is now saturated with a solution of 15% PEI for 2–10 hours, squeezed damp at the end of the saturation period and air dried.

Cationic PVA and host PVA as described above represent two materials containing cationic radicals. The charged portion of these materials act as a chelating agent, scavenger, fixative, surface charge modifier, absorbent and binder. These unique properties are capable for example of scavenging such metal ions as Nickel, Copper, Palladium, and Platinum group metals as well as halogens, particularly, Chlorine removal.

Various changes and modifications to the embodiments herein chosen for purposes of illustration will readily occur to those skilled in the art. Furthermore, while the cationic sponge is preferably used to clean hydrophobic surfaces, those skilled in the art will realize that it may be used to remove charged particles in other applications, such as for removing charged particles from water or other materials. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. A method of cleaning a surface comprising the steps of:

providing a cationic sponge material having a plurality of ionic hydroxylated polymers, containing cationic radicals, cross-linked to a plurality of hydroxylated polmers;

exposing particles and charges carried by the surface to be cleaned to the cationic radicals; and attracting and retaining particles and charges on the surface to be cleaned to the cationic radicals.

2. A method as claimed in claim 1 wherein the step of exposing further includes positioning the cationic sponge material adjacent to and in contact with the surface to be cleaned.

3. A method as claimed in claim 1 further including the step of flushing collected particles and charges from the cationic sponge using ionic reagents.

4. A method as claimed in claim 1 further including flushing the surface with at least one solution from a group containing pH reagents and miscellaneous buffers, cationic reagents, neutral reagents, anionic reagents and diluents.

* * * * *